US00PP37153P2

(12) United States Plant Patent
Smutzer

(10) Patent No.: US PP37,153 P2
(45) Date of Patent: Dec. 16, 2025

(54) LAUREL PLANT NAMED 'GREAWL'

(50) Latin Name: *Laurus nobilis*
Varietal Denomination: GREAWL

(71) Applicant: Harry Joe Smutzer, El Campo, TX (US)

(72) Inventor: Harry Joe Smutzer, El Campo, TX (US)

(73) Assignee: GREENLEAF NURSERY CO., Park Hill, OK (US)

( * ) Notice: Subject to any disclaimer, the term of this patent is extended or adjusted under 35 U.S.C. 154(b) by 0 days.

(21) Appl. No.: 19/200,404

(22) Filed: May 6, 2025

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan Mccormick Ewoldt
(74) *Attorney, Agent, or Firm* — Penny J. Aguirre

(57) ABSTRACT

A new cultivar of *Laurel* plant named 'GREAWL' that is characterized by its scalloped leaf margins creating a wavy foliage appearance, its range of leaf colors; emerging red, changing to bronze and maturing to dark green, its short internodes creating a compact plant habit, its short internodes creating a compact plant habit, its good self-branching creating a dense and full appearance, and its foliage with strong and sweet aromas of cinnamon and cloves.

3 Drawing Sheets

Botanical classification: *Laurus nobilis.*
Cultivar designation: 'GREAWL'.

BACKGROUND OF THE INVENTION

The present invention relates to a new and distinct cultivar of *Laurus nobilis* and will be referred to hereafter by its cultivar name, 'GREAWL'. 'GREAWL' is a new cultivar of bay laurel; an evergreen shrub grown for use as a landscape plant.

The new cultivar originated as a chance seedling that was discovered in a container block that had been planted with open pollinated seeds of an unnamed and unpatented plant of *Laurus nobilis* in 2019 in El Campo, Texas. The male parent is therefore unknown.

Asexual propagation of the new cultivar was first accomplished by the Inventor by semi-hardwood cuttings in April of 2021 in El Campo, Texas. Asexual propagation of the new cultivar by semi-hardwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'GREAWL' as a new and unique cultivar of *Laurel.*

1. 'GREAWL' exhibits scalloped leaf margins creating a wavy foliage appearance.
2. 'GREAWL' exhibits a range of leaf colors; emerging red, changing to bronze and maturing to dark green.
3. 'GREAWL' exhibits short internodes creating a compact plant habit.
4. 'GREAWL' exhibits good self-branching creating a dense and full appearance.

5. 'GREAWL' exhibits foliage with strong and sweet aromas of cinnamon and cloves.

The female parent of 'GREAWL' differs from 'GREAWL' in having leaf margins that are entire leaf margins, more smooth and flat leaf orientation, longer internodes, a less compact, more upright and less full plant habit, less self-branching, and young foliage that emerges mint green in color. 'GREAWL' can be most closely compared to the *Laurus nobilis* cultivars 'Crestwood' (not patented) and 'Willow Leaf' (not patented). 'Crestwood' is similar to 'GREAWL' in having dark green mature foliage. 'Crestwood' differs from 'GREAWL' in having leaves that are rounder in shape and flatter in aspect with smoother margins, and in having a larger plant size. 'Willow Leaf' is similar to 'GREAWL' in having short internodes with a compact plant habit. 'Willow Leaf' differs from 'GREAWL' in having leaves that are lighter green in color and more narrow with smoother margins, a larger plant size, a faster growth rate, and leaves that are less fragrant when crushed.

BRIEF DESCRIPTION OF THE DRAWINGS

The accompanying color photographs illustrate the overall appearance and distinct characteristics of the new *Laurel*. The photographs were taken of a plant 6 years in age of the new cultivar as grown outdoors in a 15-gallon container in El Campo, Texas.

The photograph in FIG. 1 provides a side view of the plant of 'GREAWL'.

Figure 1:
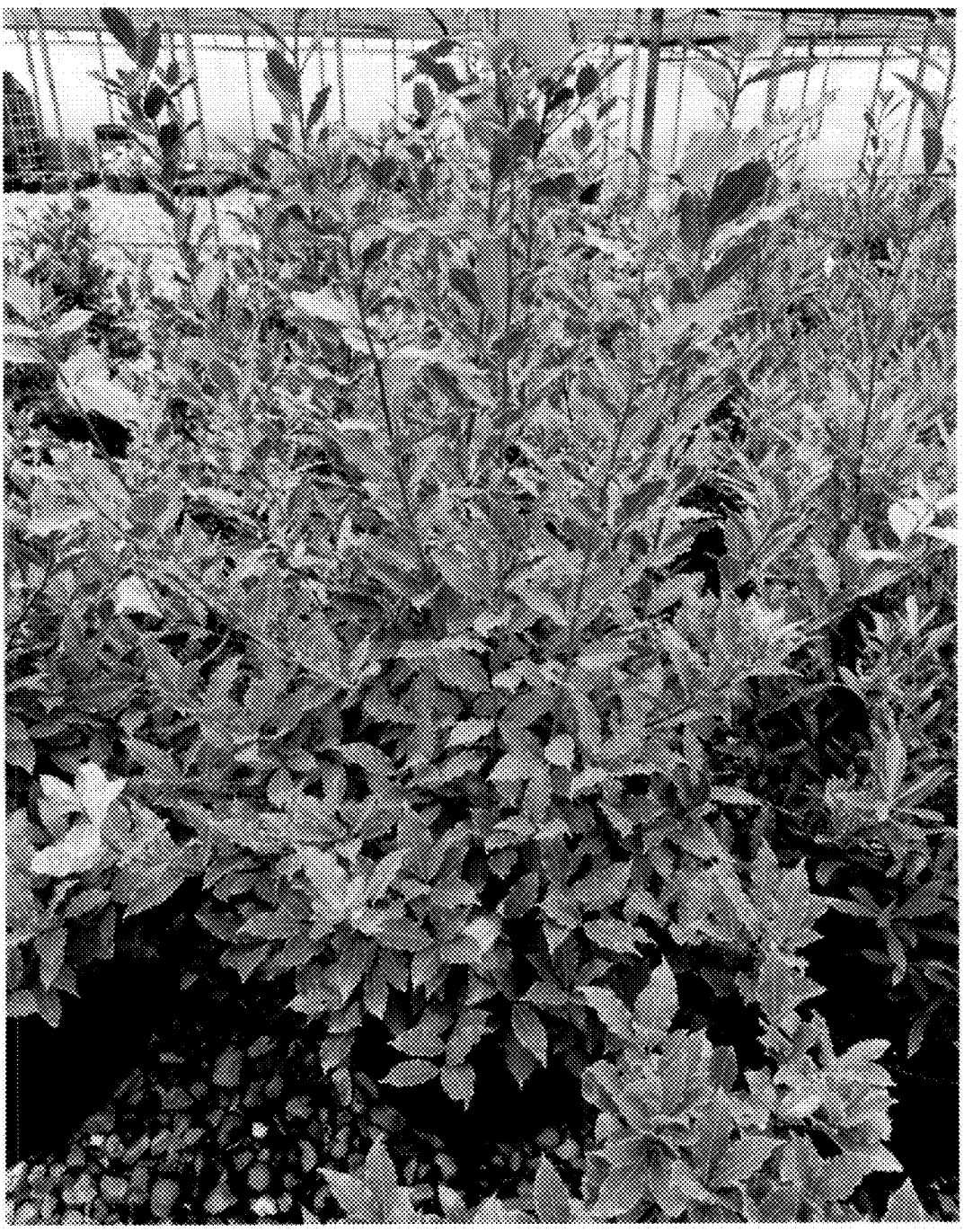
Figure 2:
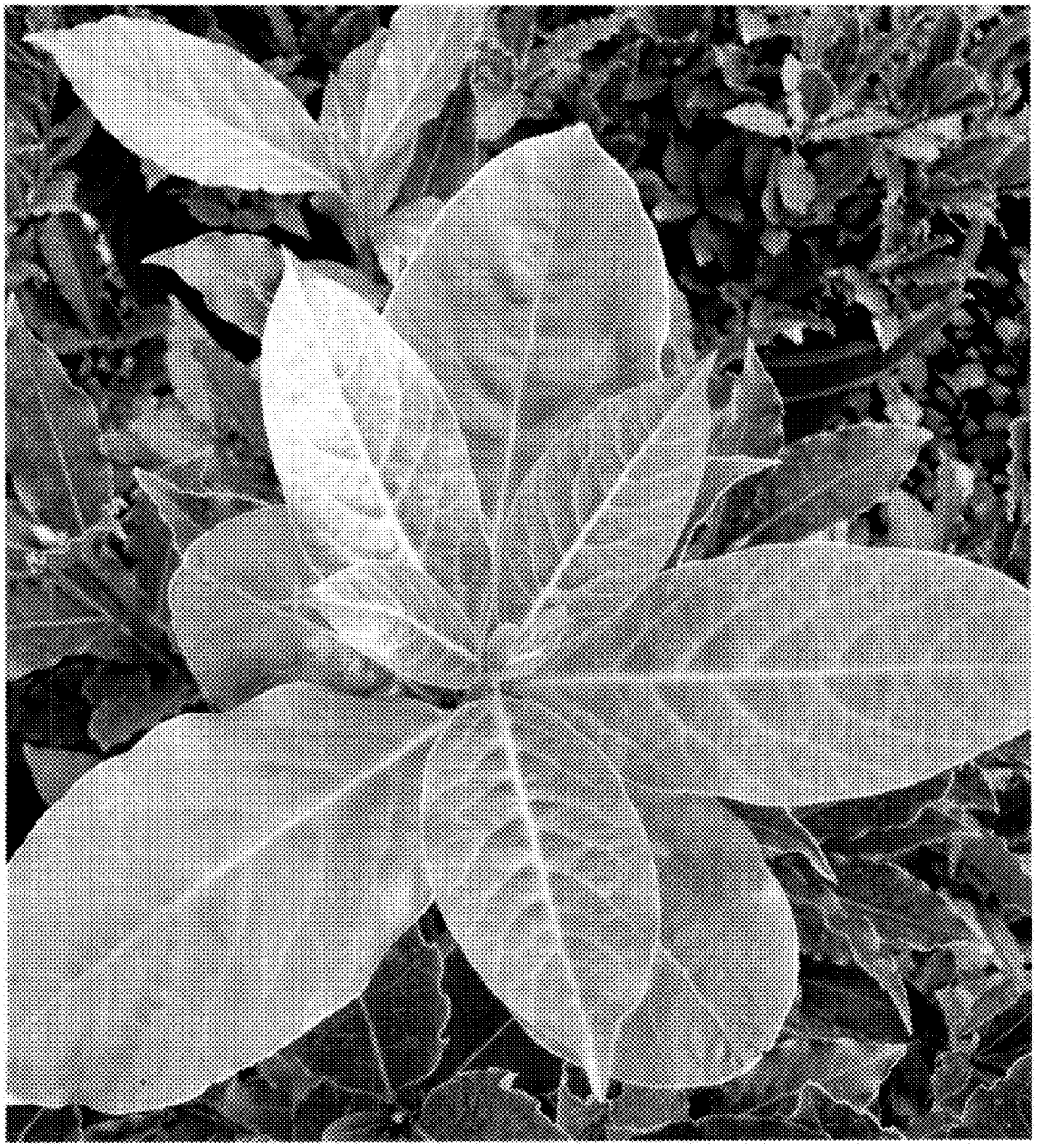

The photograph in FIG. 2 provides a close-up view of the young foliage of 'GREAWL'.

Figure 3:
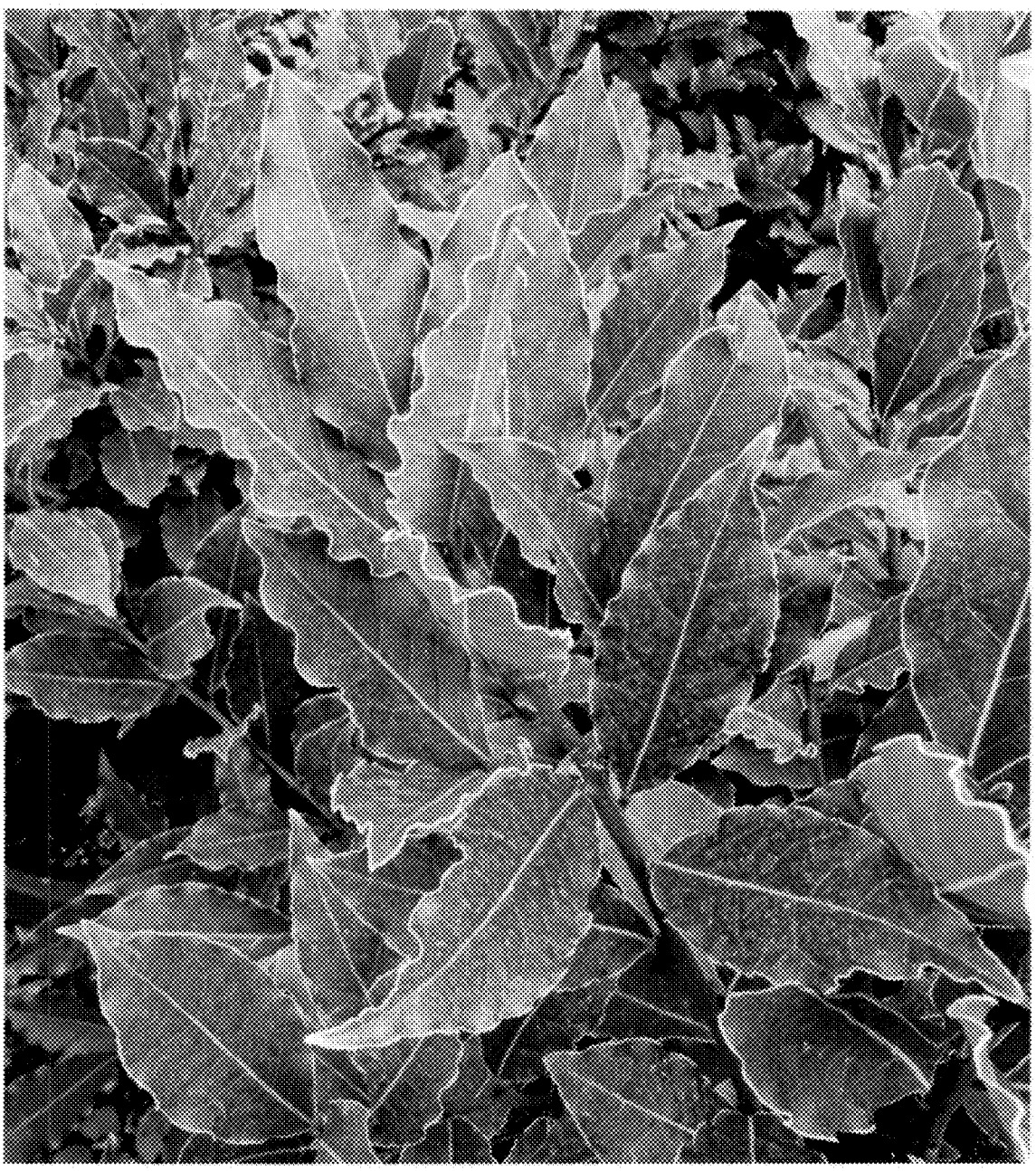

The photograph in FIG. 3 provides a close-up view of the mature foliage of 'GREAWL'.

The colors in the photographs are as close as possible with the digital photography techniques available, the color values cited in the detailed botanical description accurately describe the colors of the new *Laurel*.

DETAILED BOTANICAL DESCRIPTION OF THE PLANT

The following is a detailed description of 2.5 year-old plants of the new cultivar as grown outdoors in 3-gallon containers in Park Hill, Oklahoma. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Evergreen shrub.

*Plant habit*.—Upright, uniform, dense, and compact.

*Height and spread*.—36 cm in height and 44 cm in width as a 2.5-year-old plant grown in a container, reaches up to 4.6 m in height and 3.7 m in diameter as a mature plant in the landscape.

*Cold hardiness*.—At least in U.S.D.A. Zone 8.

*Diseases and pests*.—No susceptibility or resistance to diseases or pests has been observed, plants of *Laurel nobilis* are typically disease free.

*Root description*.—Moderately branched, 165C in color.

*Propagation*.—Semi-hardwood stem cuttings.

*Root development*.—Average of 12 weeks for root initiation, 12 to 15 months to produce a finished plant in a 1-gallon container from a rooted cutting.

*Growth rate*.—Moderate.

Branch description:

*Branch shape*.—Round.

*Branch size*.—Main; average of 25 cm in length, 1.2 cm in diameter, lateral; average of 15 cm in length, 5 mm in diameter.

*Branch surface*.—Young and maturing; glabrous, matte, wax-like coating on the surface, older and woody; covered with matte bark, very slightly rugose.

*Branch color*.—Young and maturing; 137D, older and woody; 198A in color.

*Branch strength*.—Young and maturing; strong, bendable, older and woody; very strong.

*Branch aspect*.—Branches held in a whorled aspect from the center around the main branch, held in various angles held upright to slightly bowed outward.

*Internode length*.—An average of 1 cm.

*Branching*.—Per plant; 1 main branch, 25 lateral branches.

Foliage description:

*Leaf shape*.—Elliptic to lanceolate.

*Leaf division*.—Simple.

*Leaf base*.—Attenuate.

*Leaf apex*.—Long, narrow apiculate.

*Leaf fragrance*.—Sweet, cinnamon and cloves, bay-like, suitable for culinary uses.

*Leaf venation*.—Pinnate, 145B in color on both surfaces.

*Leaf quantity*.—An average of 35 per lateral branch.

*Leaf margins*.—Crenate (scalloped), moderately undulate.

*Leaf arrangement*.—Alternate.

*Leaf aspect*.—Mature leaves typically slightly convex with veins recessed on upper

*Leaf attachment*.—Petiolate.

*Leaf surface*.—Both surfaces matte, strong and thick texture.

*Leaf size*.—Average of 6.5 cm in length and 4 cm width.

*Leaf color*.—Young leaves upper and lower surface; 34A, maturing leaves upper and lower surface 173B, turning to 144B, mature leaves upper and lower surface; 137A to 137B, margins 145B, mature color on both surfaces retained in fall and winter if good moisture.

*Petioles*.—Average of 5 cm in length and 2 mm in diameter, strong, convex, both surfaces matte, glabrous and matches leaf venation and leaf colorations.

Inflorescence description: None observed to date.

It is claimed:

1. A new and distinct cultivar of *Laurel* plant named 'GREAWL' as herein illustrated and described.

* * * * *